(12) United States Patent
Asai et al.

(10) Patent No.: US 6,449,500 B1
(45) Date of Patent: Sep. 10, 2002

(54) PROBE FOR OPTICAL MEASUREMENT

(75) Inventors: Kuniharu Asai; Naoki Yanai; Motonobu Shiomi; Nobuyoshi Yasuda, all of Osaka (JP)

(73) Assignee: Kurabo Industries Ltd., Okayama (JP)

( * ) Notice: Subject to any disclaimer, the term of this patent is extended or adjusted under 35 U.S.C. 154(b) by 228 days.

(21) Appl. No.: 09/620,573

(22) Filed: Jul. 20, 2000

(30) Foreign Application Priority Data

Jul. 23, 1999 (JP) .............................. 11-209923

(51) Int. Cl.$^7$ .............................................. A61B 5/00
(52) U.S. Cl. ................... 600/310; 250/227.28; 600/335
(58) Field of Search ................................ 600/310, 322, 600/323, 344, 473, 475, 476, 335; 385/45, 47; 250/227.11, 227.23, 227.28; 356/39, 41

(56) References Cited

U.S. PATENT DOCUMENTS

| | | | |
|---|---|---|---|
| 4,295,470 A | * 10/1981 | Shaw et al. | 600/339 |
| 5,185,834 A | * 2/1993 | Day et al. | 385/47 |
| 5,298,741 A | * 3/1994 | Walt et al. | 250/227.23 |
| 5,396,079 A | * 3/1995 | Evers et al. | 250/227.28 |
| 5,513,642 A | * 5/1996 | Ostrander | 600/334 |
| 5,800,350 A | * 9/1998 | Coppleson et al. | 600/475 |
| 5,827,181 A | * 10/1998 | Dias et al. | 600/322 |

* cited by examiner

*Primary Examiner*—Eric F. Winakur
(74) *Attorney, Agent, or Firm*—Rader, Fishman & Grauer PLLC

(57) ABSTRACT

A second optical component is an optical fiber bundle charged in a clearance between an inner cylinder and an outer cylindrical outer peripheral part in the form of a ring. These elements are integrated with each other, and forward-end-surfaces thereof are on concentric circles. A ring of the forward-end-surface of the outer peripheral part is larger in width than the ring of the forward-end-surface of the second optical component. A first optical component charged with an optical fiber bundle is slidably inserted into and engaged in the cylinder inside the second optical component, so that the forward-end-surface of the first optical component can project or retract from the forward-end-surface of the outer peripheral part. The outer peripheral part is brought into contact with a human body and force for pressing a measured region is changed by sliding the first optical component for measuring absorption spectra between the first and second optical components under different values of pressing force, thereby obtaining a difference absorbance spectrum under different states of pressurization.

9 Claims, 7 Drawing Sheets

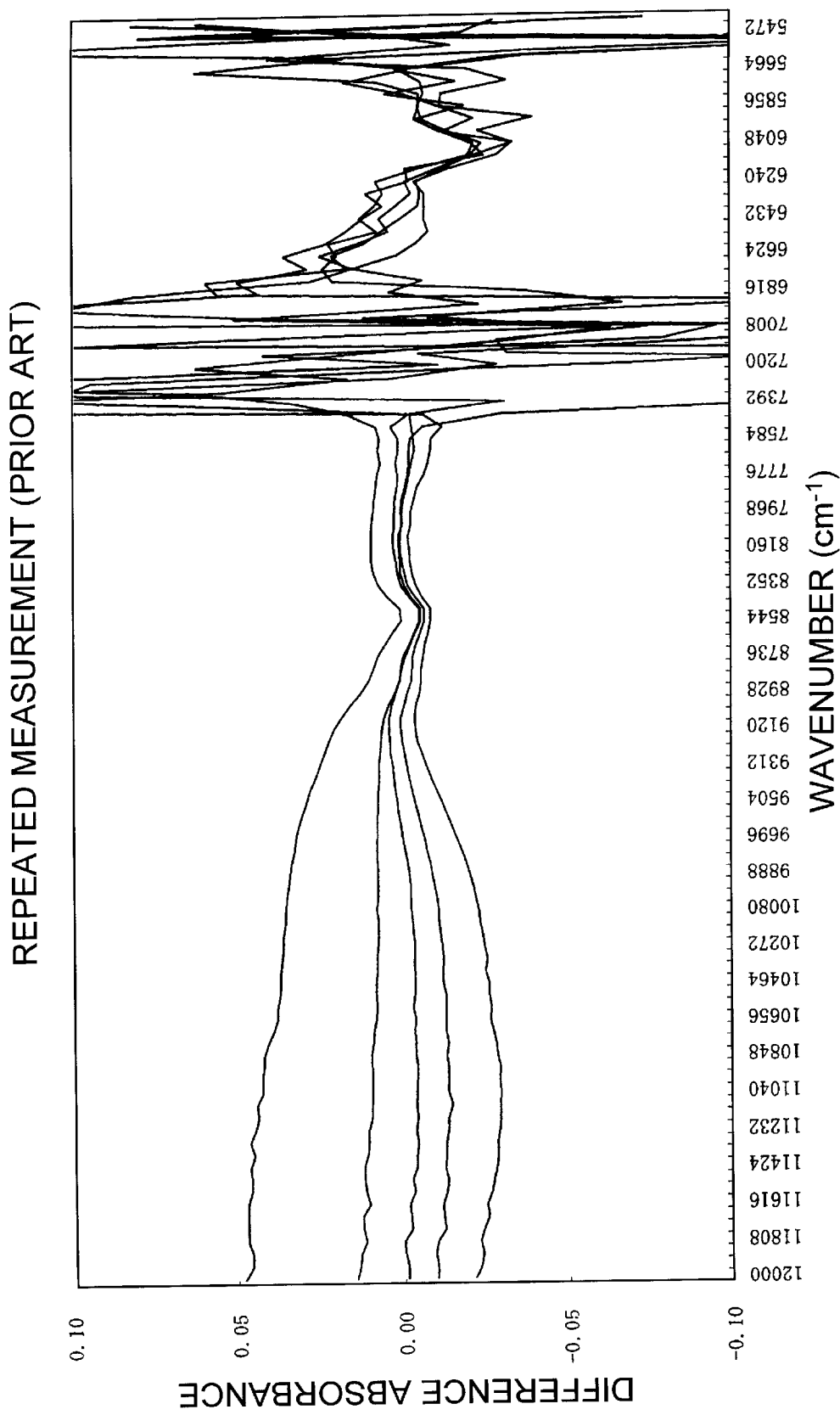
Fig. 7 REPEATED MEASUREMENT (PRIOR ART)

PROBE FOR OPTICAL MEASUREMENT

BACKGROUND OF THE INVENTION

1. Field of the Invention

The present invention relates to a probe for projecting measuring light to an organism and receiving output light from the organism through the measuring light for non-invasively measuring kinds of physical quantity of a vital tissue. This probe is used for irradiating, for example, a human body with light of a near-infrared region and measuring kinds of physical quantity in the human body such as a glucose concentration in blood, oxygen saturation of blood, body fat or an abnormal tissue by output light from the human body.

2. Description of the Prior Art

In the field of clinical testing, there is made an attempt of irradiating an organism with light and receiving the light penetrating into the organism to be scattered or reflected therein and outgoing from the organism for measuring an oxygen saturation in blood or a blood-sugar level or obtaining a body fat rate. There is also made another attempt of detecting an abnormal tissue from change of reflection properties responsive to the strength of a pressure by controlling the pressure pressing a probe for transmitting/receiving light to/from an organism against the organism.

As a first method of pressurizing a measured portion in measurement of an organism, a method of putting a cuff of a finger-blood-pressure-gauge on a finger and controlling an air pressure fed to the cuff thereby congesting a measured portion is proposed (refer to Japanese Patent Laying/Open Gazette No. 1-146525 (1989)).

As a second method, a method of slidably inserting an optical fiber bundle for transmitting/receiving measuring light into a tube and interposing a spring between the optical fiber bundle and the tube thereby pressurizing an organism with the optical fiber bundle through the force of the spring or introducing a transparent body for transmitting/receiving measuring light into a tube and pressurizing the same with an air pressure thereby pressurizing an organism with the transparent body is proposed (refer to Japanese Patent Publication Gazette No. 60-43134 (1985)).

The first method is limited to only measurements of a finger, and cannot be applied to measurements of a wide area portion of a human body.

In the second method, the pressure for pressing the optical fiber bundle or the transparent body for transmitting/receiving light against the organism can be controlled through the spring or the air pressure. However, the area of the forward-end-surface of the tube supporting the optical fiber bundle or the transparent body is small, and contact with the organism is mainly made on the forward-end-surface of the optical fiber bundle or the transparent body for transmitting/receiving light The area of this forward-end-surface is also small, and hence, only the measured portion is pressurized. Thus, it is difficult to stabilize the degree of application of the pressure to a portion around the measured portion.

When pressurized, an organism such as a human body may be congested or may lose a large quantity of blood depending on the degree of pressurization or influence by a contact area. In either case, reproducibility of the state as well as reproducibility of a result of measurement is reduced when the contact area is small.

SUMMARY OF THE INVENTION

Accordingly, an objective of the present invention is to improve reproducibility of measurement by keeping a degree of application of a pressure to a region including a measured region and its periphery.

A probe for optical measurement according to the present invention comprises a first optical component arranged on a central axis having a flat circular forward-end-surface and a second optical component having a flat forward-end-surface arranged in the form of a ring on a circle surrounding the central axis outside the first optical component, and these optical components are engaged with each other to be relatively slidable in the axial direction. One of the optical components is a projecting part projecting measuring light to a measured object, and the other optical component is a photoreceiving part receiving output light from the measured object through the projected measuring light The probe for optical measurement further comprises an outer peripheral part having a forward-end-surface in the form of a ring on a circle surrounding the central axis outside the second optical component, and the ring is formed to be larger in width than the ring of the forward-end-surface of the second optical component.

The projecting part and the photoreceiving part are independent of each other and the photoreceiving part is arranged to enclose the projecting part or the projecting part is arranged to enclose the photoreceiving part to the contrary, whereby information on a deep place of an organism can be readily obtained as compared with a probe having a projecting part and a photoreceiving part located on the same place as a transmission/photoreceiving part.

The wide outer peripheral part is provided outside the second optical component, whereby the degree of application of a pressure to a wide portion around the measured region can be kept constant by bringing the outer peripheral part into contact with the organism. A contact pressure in a narrow range of the measured region can be changed with the first optical component, whereby reproducibility of change of a tissue component such as change of a blood component in the measured region can be improved.

The output light from the measured object received by the photoreceiving part includes all light output from the measured object such as transmitted light, scattered light and reflected light after projection of the light to the measured object.

The outer peripheral part is integrated with the second optical component so that the forward-end-surfaces of the outer peripheral part and the second optical component can be flush with each other. Thus, measurement can be made in a state bringing the forward-end-surface of the second optical component into contact with the measured region along with the outer peripheral part.

The outer peripheral part is alternatively integrated with the second optical component so that the forward-end-surface of the second optical component may be located in a vertical position retracted from the forward-end-surface of the outer peripheral part Thus, measurement can be made in a state not bringing the forward-end-surface of the second optical component into contact with the measured region, for reducing influence exerted by the probe on the measured region.

The projecting part can be a light-guide-path guiding the measuring light from a light source. In this case, the degree of freedom in light source selection is improved, wavelength selection is easy and it is also easy to attain high luminous energy. It is also possible to provide a spectroscope between the light source and the light-guide-path.

The projecting part alternatively can be provided with a light emitting device such as an LED (light emitting diode)

or an LD (laser diode) embedded therein. In this case, it is advantageous for miniaturizing the probe.

The photoreceiving part can be a light-guide-path such as an optical fiber bundle guiding the received output light to a detector. In this case, the degree of freedom in detector selection is improved. It is also possible to provide a spectroscope between the light-guide-path and the detector.

The photoreceiving part alternatively can be provided with a photoreceiving element such as a photodiode or a phototransistor embedded therein. In this case, it is advantageous for miniaturizing the probe.

When arranging the photoreceiving part to enclose the projecting part, it is possible to efficiently receive the output light from the organism, and detection sensitivity is improved.

In order to measure kinds of physical quantity of a vital tissue, light from near-infrared to infrared regions is preferable. The light source being used, emitting light included in such a wavelength region, may include a continuous spectrum of this wavelength region or discontinuous bright line spectra. Such a light source may be formed by an LED or an LD for near-infrared or infrared emission, in addition to a tungsten-halogen lamp.

The detector or the photoreceiving element has sensitivity to the near-infrared or infrared region, and such an infrared detector can be formed by a Ge photodiode, an InGaAs photodiode, a PbS photoconductive element, a PbSe photoconductive element, an InAs photovoltaic element or a pyroelectric element.

It is possible to keep a contact pressure on the measured region constant for improving reproducibility of a result of measurement by making the distance of relative projection or retraction of the first optical component in the axial direction constant with respect to the outer peripheral part. To this end, a mechanism slidably engaging and supporting the optical components is preferably provided with a stopper relatively positioning the optical components on such a position that the forward-end-surface of one of the optical components projects by a constant distance with respect to the forward-end-surface of the other optical component.

The foregoing and other objects, features, aspects and advantages of the present invention will become more apparent from the following detailed description of the present invention when taken in conjunction with the accompanying drawings.

BRIEF DESCRIPTION OF THE DRAWINGS

FIG. 7 is a waveform diagram showing difference absorbance spectra in the near-infrared region repeatedly measured while making it possible to pressurize a measured region by another method.

DESCRIPTION OF THE PREFERRED EMBODIMENTS

Figure 1A:
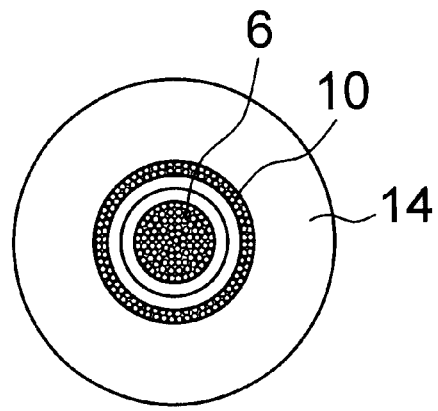
FIGS. 1A and 1B are a plan view and a partially fragmented front elevational view showing an embodiment of the present invention with a first optical component projecting from a second optical component respectively.
Figure 1B:
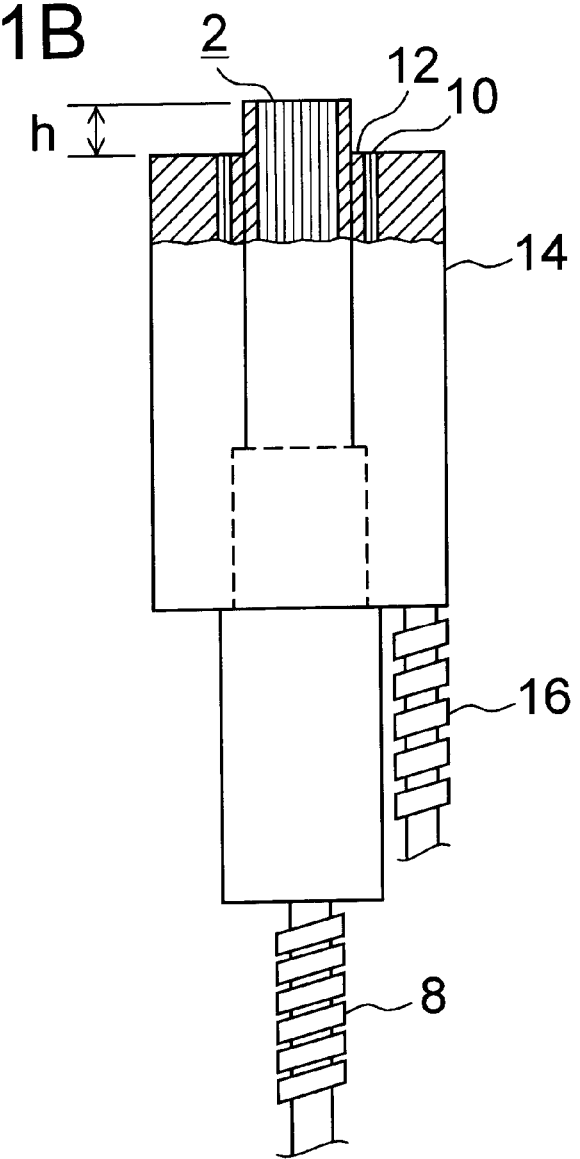
Figure 2A:
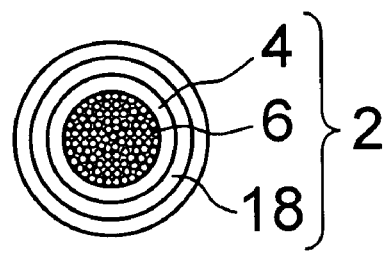
FIGS. 2A and 2B are a plan view and a front elevational view showing the first optical component in the embodiment respectively.
Figure 2B:
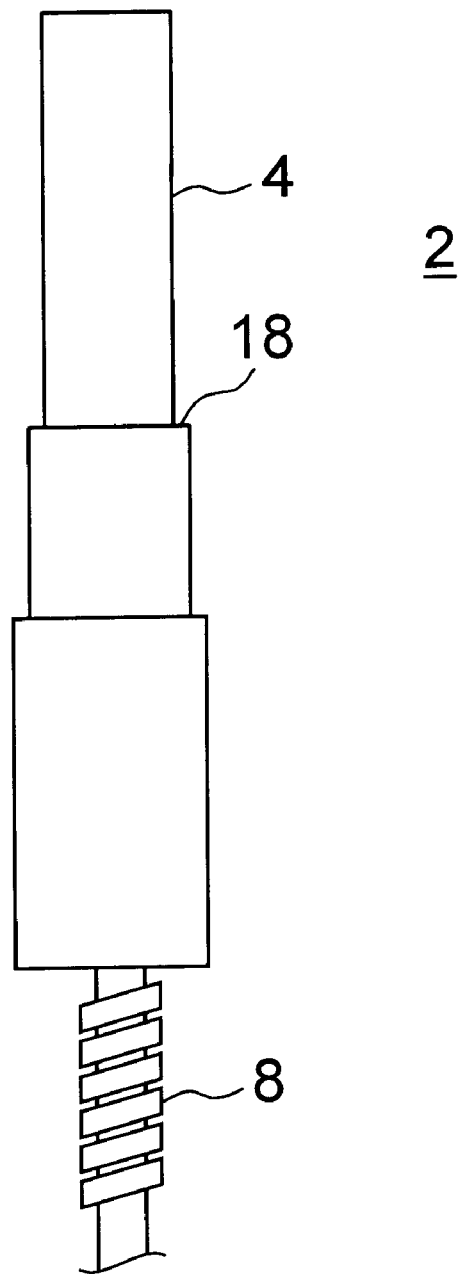
Figure 3A:
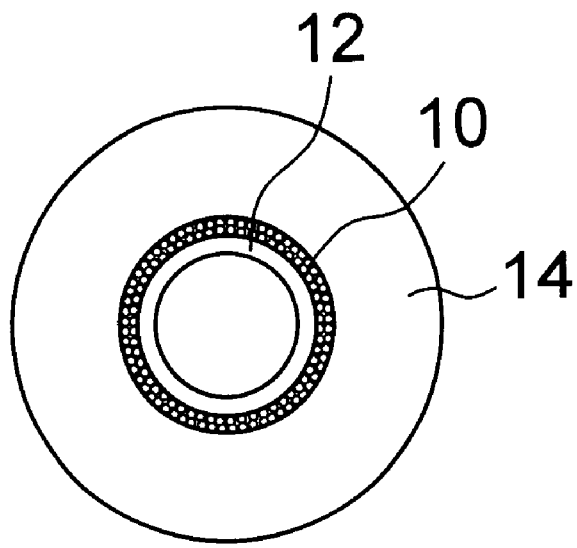
FIGS. 3A and 3B are a plan view and a front elevational view showing the second optical component in the embodiment along with an outer peripheral part respectively.
Figure 3B:
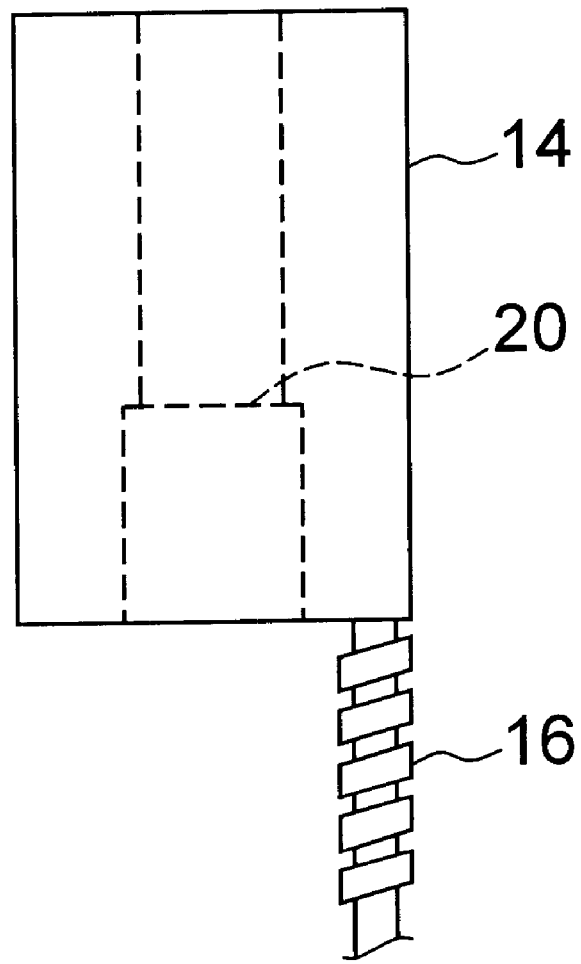

FIGS. 1A and 1B are a plan view and a partially fragmented front elevational view showing an embodiment of the present invention with a first optical component 2 projecting from a second optical component 10 respectively. FIGS. 2A and 2B are a plan view and a front elevational view showing the first optical component 2 in the embodiment respectively. FIGS. 3A and 3B are a plan view and a front elevational view showing the second optical component 10 in the embodiment along with an outer peripheral part 14.

The first optical component 2 located on a central axis is prepared by charging a cylinder 4 with an optical fiber bundle 6 so that forward-end-surfaces of the cylinder 4 and the optical fiber bundle 6 are flush with each other. The optical fiber bundle 6 is supported by a bendable mantle 8 on a portion closer to a base end than the cylinder 4, and guided to an external measuring apparatus with flexibility.

The second optical component 10 is also an optical fiber bundle charged in a clearance between an inner cylinder 12 and an outer cylindrical outer peripheral part 14 in the form of a ring. The cylinder 12, the second optical component 10 and the outer peripheral part 14 are integrated with each other, the forward-end-surfaces of these members are formed as rings for defining concentric circles, and the ring of the forward-end-surface of the outer peripheral part 14 is larger in width than the ring of the forward-end-surface of the second optical component 10. The optical fiber bundle of the second optical component 10 is supported by a bendable mantle 16 on a portion closer to a base end than the outer peripheral part 14, and guided to the external measuring apparatus with flexibility.

As shown in FIGS. 1A and 1B, the first optical component 2 is slidably inserted into and engaged in the cylinder 12 inside the second optical component 10, so that the forward-end-surface of the first optical component 2 can project or retract from that of the outer peripheral part 14. The outer diameter of the first optical component 2 and the inner diameter of the cylinder 12 are so set that the first optical component 2 is axially slidable without radial displacement In order to render the height of projection of the first optical component 2, a step 18 is formed on the outer peripheral surface of the first optical component 2 by increasing the diameter on the base end side while a step 20 is formed on the inner peripheral surface of the cylinder 12 by increasing the diameter on the base end side in correspondence thereto. The steps 18 and 20 form stoppers. When inserting and engaging the first optical component 2 into and in the cylinder 12, sliding is stopped in such a state that the step 18 hits the step 20. In the state shown in FIG. 1B stopping sliding, the positions of the steps 18 and 20 are so set that the forward-end-surface of the first optical component 2 projects from that of the outer peripheral part 14 by a desired height "h" of, for example, 1 mm.

The materials for the cylinders 4, 12 and the outer peripheral part 14 are not particularly restricted but preferably prepared from a metal such as stainless steel in view of durability.

As to exemplary dimensions of the forward-end-surfaces of these elements, the diameter of the optical fiber bundle 6 of the first optical component 2 is 1 to 10 mm, e.g., 5 mm, the outer diameter and the width of the second optical component 10 are 5 to 15 mm, e.g., 11.2 mm and 1 to 3 mm, e.g., 1 mm respectively, and the outer diameter and the width of the outer peripheral part 14 are 30 to 100 mm, e.g., 40 mm and 20 to 80 mm, e.g., 21.5 mm respectively. However, the present invention is not restricted to these dimensions, as a matter of course.

A measuring method employing this embodiment shall now be described.

(1) The first optical component 2 is inserted into and engaged in the cylinder 12 so that the forward-end-surfaces of the first optical component 2 and the outer peripheral part 14 are flush with each other, for bringing this probe into contact with a human body.

First, the optical fiber bundle 6 of the first optical component 2 projects measuring light in a state not pressurizing the human body, and the measuring light penetrates into the human body, going out from the human body and entering the optical fiber bundle of the second optical component 10 to the measuring apparatus for measuring its absorption spectrum.

Figure 4A:
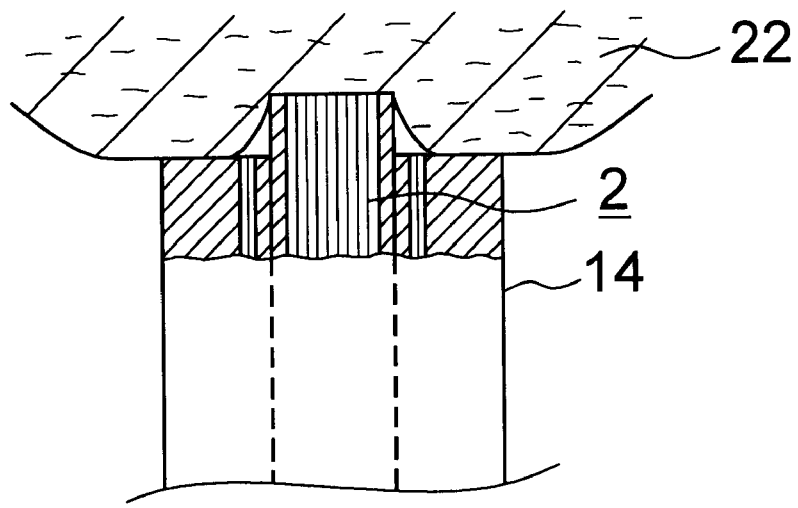
FIGS. 4A and 4B are partial sectional views showing a state pressurizing a measured region by projecting the forward-end-surface of the first optical component and a state pressurizing the periphery of the measured region by retracting the forward-end-surface of the first optical component.

(2) Next, the first optical component 2 is pushed toward the forward end into such a position that the step 18 hits the step 20. In this state, the forward-end-surfaces of the second optical component 10, the cylinder 12 and the outer peripheral part 14 come into contact with the human body in an unpressurized state and the forward-end-surface of the first optical component 2 located at the center projects by the height "h", thereby attaining contact while only the forward-end-surface of the optical component 2 pressurizes a measured region of the human body. FIG. 4A shows this contact state, with numeral 22 denoting a human body such as the palm. An absorption spectrum is measured in this state similarly to (1).

Thereafter, the difference (difference absorbance spectrum) between the absorption spectra obtained in (1) and (2) is obtained. Absorption spectra in the near-infrared region reflect various components such as a blood component forming a human tissue and others. When obtaining a difference absorbance spectrum according to the present invention, influence by a component not changed by pressurization is so eliminated that an absorbance spectrum reflecting a component changed by pressurization, mainly a blood component, can be obtained.

Figure 4B:
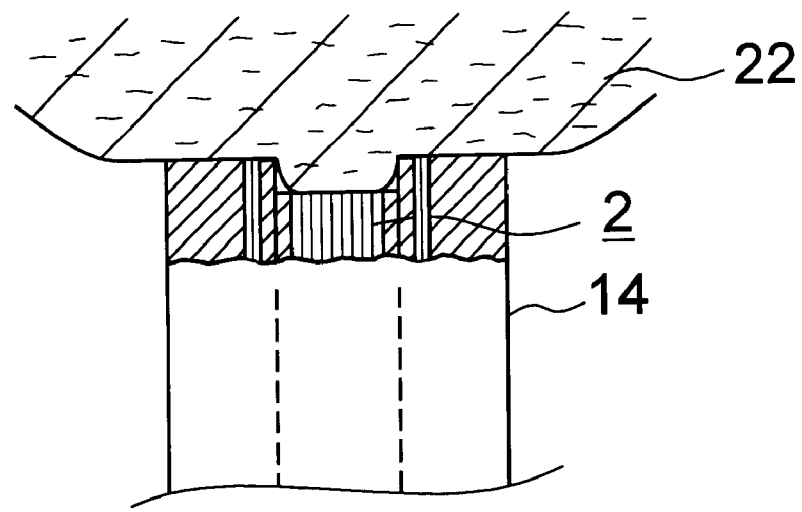
Figure 5:
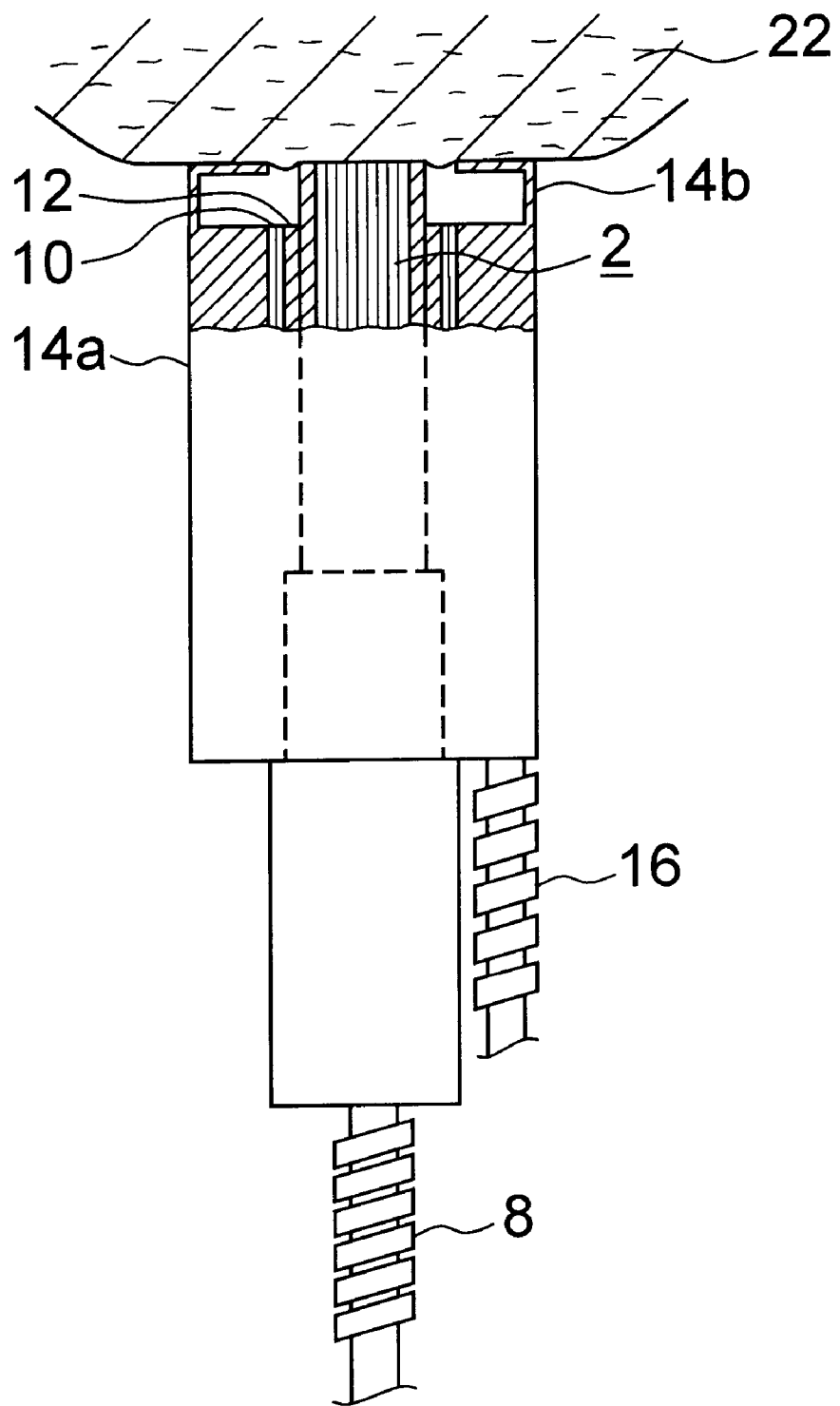
FIG. 5 is a partially fragmented front elevational view showing another embodiment.

As the measuring method, it is possible to make measurement by bringing the probe into contact with the measured region while retracting the forward-end-surface of the optical component 2 from that of the outer peripheral part 14 by a prescribed distance, in place of the aforementioned method of projecting the forward-end-surface of the first optical component 2 from that of the outer peripheral part 14 by a prescribed distance. FIG. 4B shows this contact state. In this case, measurement can be made in a state not pressurizing a region coming into contact with the forward-end-surface of the first optical component 2 but pressurizing a peripheral portion of the measured region with the forward-end-surfaces of the second optical component 10, the cylinder 12 and the outer peripheral part 14. In other words, a spectrum of a tissue component changed on the measured region can be obtained by changing a contact pressure around the measured region. While the optical fiber bundle 6 on the central portion projects the measuring light and the optical fiber bundle of the second optical component 10 on the peripheral portion receives the measuring light in the embodiment, the optical fiber bundle of the second optical component 10 on the peripheral portion may alternatively project measuring light so that the optical fiber bundle 6 receives the measuring light FIG. 5 shows another embodiment Dissimilarly to the embodiment shown in FIGS. 1A and 1B, an outer peripheral part 14a integrated with a second optical component 10 includes a wide ring-shaped cap 14b coming into contact with a measured region on its front portion. The forward-end-surface of the second optical component 10 is fixed on a vertical position retracted from the cap 14b by a constant distance.

In this embodiment, absorption spectra are measured in two of three states including a state bringing the cap 14b into contact with a peripheral portion of the measured region and projecting the forward-end-surface of the first optical component 2 from the cap 14b, a state rendering the forward-end-surface flush with the cap 14b, and a state retracting the forward-end-surface from the cap 14b, for obtaining a difference absorbance spectrum. At this time, the forward-end-surface of the second optical component 10 is not in contact with the measured region, at least, and hence measurement can be made in a state reducing influence exerted by a probe on the measured region.

In place of the optical fiber bundle projecting the measuring light, a light emitting device such as a light emitting diode or a laser diode may be embedded in and arranged on the projecting side.

In place of the optical fiber bundle on the photoreceiving side, a photoreceiving element such as a photodiode or a phototransistor can be arranged and embedded.

Results of measurement in the embodiment shall now be described.

Figure 6:
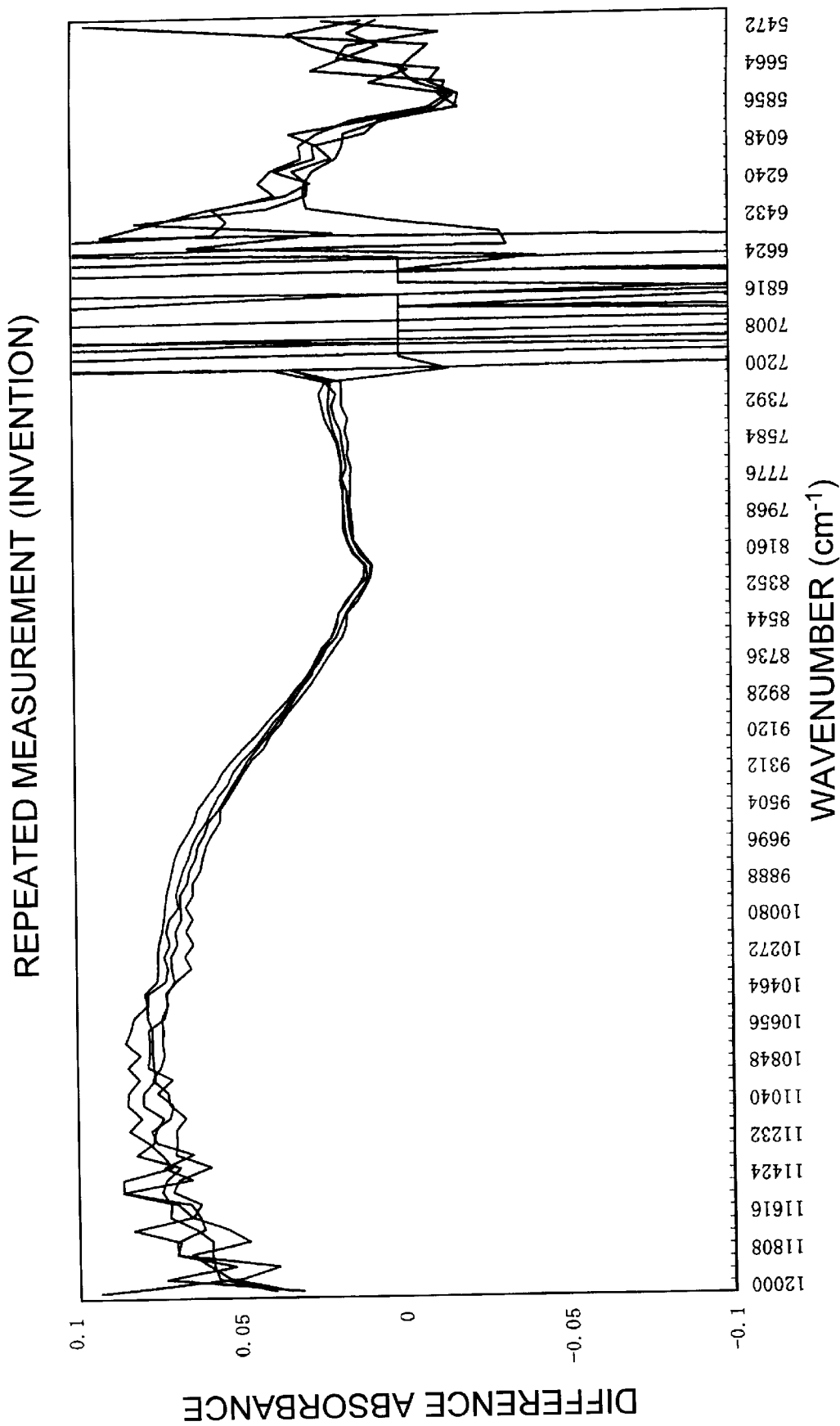
FIG. 6 is a waveform diagram showing difference absorbance spectra in the near-infrared region repeatedly measured with a probe according to the embodiment shown in FIGS. 1A and 1B.

FIG. 6 shows results obtained by employing the probe according to the embodiment shown in FIGS. 1A and 1B for measuring an absorption spectrum in an unpressurized state in the near-infrared region and an absorption spectrum in a state (pressurized state) projecting the forward-end-surface of the first optical component 2 from the forward-end-surface of the outer peripheral part 14 determined by the stoppers and obtaining a difference absorbance spectrum from these absorbance spectra. This measurement was repeated four times. Turbulence of the spectra around 7000 cm resulted from influence by water. In this measurement, fluctuation for each individual time is small and it is understood that reproducibility is excellent As a comparative example, a measured region was pressurized with another means for similarly measuring absorption spectra. An air pack was employed as pressurization means. Absorption spectra were measured in an unpressurized state and a state pressurizing the measured region with a constant air pressure respectively, for obtaining a difference absorption spectrum from these absorption spectra. FIG. 7 shows results obtained by repeating this measurement five times. In the pressurization method according to this comparative example, the spectra fluctuate every measurement to indicate that this method is inferior in reproducibility to the pressurization method according to the present invention.

Although the present invention has been described and illustrated in detail, it is clearly understood that the same is by way of illustration and example only and is not to be taken by way of limitation as the spirit and scope of the present invention are limited only by the terms of the appended claims.

What is claimed is:

1. A probe for optical measurement, comprising:

a first optical component, arranged on a central axis, having a flat circular forward-end-surface;

a second optical component having a flat forward-end-surface arranged in the form of a ring on a circle surrounding said central axis outside said first optical component; and an outer peripheral part having a forward-end-surface in the form of a ring on a circle surrounding said central axis outside said second optical component, said ring being formed to be larger in width than said ring of said forward-end-surface of said second optical component, wherein said optical components are engaged with each other to be relatively slidable in the axial direction, one of said optical components is a projecting part projecting measuring light to a measured object, and the other said optical component is a photoreceiving part receiving output light from said measured object through said projected measuring light.

2. The probe for optical measurement according to claim 1, wherein said outer peripheral part is integrated with said second optical component so that said forward-end-surfaces of said outer peripheral part and said second optical component are flush with each other.

3. The probe for optical measurement according to claim 1, wherein said outer peripheral part is integrated with said second optical component so that said forward-end-surface of said second optical component is on a vertical position retracted from said forward-end-surface of said outer peripheral part.

4. The probe for optical measurement according to claim 1, wherein said projecting part is a light-guide-path guiding said measuring light from a light source.

5. The probe for optical measurement according to claim 1, wherein said projecting part is provided with a light emitting device embedded therein.

6. The probe for optical measurement according to claim 1, wherein said photoreceiving part is a light-guide-path guiding received output light to a detector.

7. The probe for optical measurement according to claim 1, wherein said photoreceiving part is provided with a light dectecting device embedded therein.

8. The probe for optical measurement according to claim 1, wherein said first optical component is said projecting part, and said second optical component is said photoreceiving part.

9. The probe for optical measurement according to claim 1, wherein a mechanism slidably engaging and supporting said optical components is provided with a stopper relatively positioning said optical components on such a position that said forward-end-surface of one of said optical components projects from said forward-end-surface of the other said optical component by a constant distance.

* * * * *